(12) United States Patent
Chen et al.

(10) Patent No.: US 11,259,995 B2
(45) Date of Patent: Mar. 1, 2022

(54) DENTAL COMPOSITIONS AND METHODS OF USE

(71) Applicant: ZEST IP HOLDINGS, LLC, Carlsbad, CA (US)

(72) Inventors: Xiangxu Chen, Diamond Bar, CA (US); Matthew Marc Durban, Fullerton, CA (US)

(73) Assignee: ZEST IP HOLDINGS, LLC, Carlsbad, CA (US)

( * ) Notice: Subject to any disclaimer, the term of this patent is extended or adjusted under 35 U.S.C. 154(b) by 0 days.

(21) Appl. No.: 15/331,176

(22) Filed: Oct. 21, 2016

(65) Prior Publication Data

US 2017/0035662 A1 Feb. 9, 2017

Related U.S. Application Data

(63) Continuation of application No. PCT/US2016/016901, filed on Feb. 5, 2016.
(Continued)

(51) Int. Cl.
*A61K 6/887* (2020.01)
*A61C 5/00* (2017.01)
(Continued)

(52) U.S. Cl.
CPC ............... *A61K 6/887* (2020.01); *A61C 5/00* (2013.01); *A61K 6/17* (2020.01); *A61K 6/60* (2020.01);
(Continued)

(58) Field of Classification Search
CPC .... A61K 6/0047; A61K 6/083; A61K 6/0088; A61K 6/0276; A61K 6/04; A61K 6/0008; A61K 6/0091; A61K 6/025; A61K 6/887; A61K 6/77; A61K 6/836; A61K 6/76; A61K 6/60; A61K 6/822; A61K 6/84; A61K 6/17; A61C 5/00
(Continued)

(56) References Cited

U.S. PATENT DOCUMENTS 3,991,008 A 11/1976 Temin et al.
4,629,746 A 12/1986 Michl et al.
(Continued)

FOREIGN PATENT DOCUMENTS

CA 2551973 A1 2/2007
CN 101129295 A 2/2008
(Continued)

OTHER PUBLICATIONS

International Search Report and Written Opinion for PCT2016016901, dated May 17, 2016 (14 pages).
(Continued)

*Primary Examiner* — Heidi M Eide
(74) *Attorney, Agent, or Firm* — Procopio, Cory, Hargreaves & Savitch LLP

(57) ABSTRACT

Provided herein are high performance dental restoration compositions, particularly two-part compositions having good self-cure times. Also provided herein are methods for restoring or filling a cavity in a tooth in an individual with the two-part dental restoration compositions. In particular, compositions provided herein are useful in restoring large cavities, including Class I and Class II cavities.

11 Claims, 2 Drawing Sheets

Related U.S. Application Data

(60) Provisional application No. 62/260,193, filed on Nov. 25, 2015, provisional application No. 62/113,899, filed on Feb. 9, 2015.

(51) Int. Cl.
*A61K 6/17* (2020.01)
*A61K 6/60* (2020.01)
*A61K 6/76* (2020.01)
*A61K 6/77* (2020.01)
*A61K 6/84* (2020.01)
*A61K 6/822* (2020.01)
*A61K 6/836* (2020.01)

(52) U.S. Cl.
CPC .................. *A61K 6/76* (2020.01); *A61K 6/77* (2020.01); *A61K 6/822* (2020.01); *A61K 6/836* (2020.01); *A61K 6/84* (2020.01)

(58) Field of Classification Search
USPC ................................................ 523/115–118
See application file for complete search history.

(56) References Cited

U.S. PATENT DOCUMENTS

| | | | |
|---|---|---|---|
| 8,552,088 B2 | 10/2013 | Shinoda et al. | |
| 8,915,736 B2 | 12/2014 | Blomker et al. | |
| 2004/0242817 A1* | 12/2004 | Kendall | C09J 4/00 526/217 |
| 2006/0189728 A1* | 8/2006 | Qian | A61K 6/0023 524/99 |
| 2007/0040151 A1* | 2/2007 | Utterodt | A61K 6/0017 252/182.13 |
| 2007/0100019 A1* | 5/2007 | Sun | A61K 6/0017 523/116 |
| 2009/0208909 A1 | 8/2009 | Rusin et al. | |
| 2010/0041786 A1* | 2/2010 | Qian | A61K 6/083 522/154 |
| 2011/0315928 A1* | 12/2011 | Jin | A61K 6/887 252/301.35 |
| 2013/0004418 A1* | 1/2013 | Neander | A61K 6/002 424/1.61 |
| 2013/0274426 A1 | 10/2013 | Sugiura et al. | |

FOREIGN PATENT DOCUMENTS

| | | |
|---|---|---|
| EP | 0710475 A1 | 8/1996 |
| GB | 2075035 A | 11/1981 |
| JP | S56-169609 A | 12/1981 |
| JP | S61-171404 A | 8/1986 |
| JP | H08-208417 A | 8/1996 |
| JP | 2002-518309 A | 6/2002 |
| JP | 2007-56020 A | 3/2007 |
| JP | 2009-503086 A | 1/2009 |
| JP | 2010-540546 A | 12/2010 |
| WO | 86/003404 A1 | 6/1986 |
| WO | 9965453 A1 | 12/1999 |
| WO | 2007016508 A1 | 2/2007 |
| WO | 2009042574 A1 | 4/2009 |

OTHER PUBLICATIONS

Chuang et al., Effects of lining materials on microleakage and internal voids of Class II resin-based composite restorations. American Journal of Dentistry, 2003, vol. 16, No. 2, p. 84-90: (Figure 1).
Munhoz et al., "Evaluation of proximal enamel thickness and crown measurements in maxillary first premolars", o Brazilian Journal of Oral Science, 2012, vol. 11, No. 1, p. 30-35: (Table 1).
European Supplemental Search Report for EP 16749641 dated Sep. 10, 2018, 9 pages.
Chinese Office Action dated Nov. 15, 2019 for corresponding application CN2016800067795, (7 pages).
Japanese Office Action dated Nov. 28, 2019 for corresponding application JP2017541824, (8 pages).
Japanese Office Action dated Sep. 25, 2020 for corresponding Application No. 2017-541824 in 23 pages.

* cited by examiner

DENTAL COMPOSITIONS AND METHODS OF USE

CROSS-REFERENCE

This application is a continuation of PCT/US2016/016901, filed on Feb. 5, 2016, which claims the benefit under 35 U.S.C 119(e) to U.S. Provisional Application No. 62/113,899, filed Feb. 9, 2015, and 62/260,193, filed Nov. 25, 2015, and the disclosure of each of the aforementioned applications is incorporated herein by reference in its entirety.

FIELD OF THE INVENTION

The field of use is dental compositions, particularly those useful in dental restoration applications, as well as methods of restoring a tooth using the dental compositions.

BACKGROUND OF THE INVENTION

A dental restoration or dental filling is a dental restorative material used to restore the function, integrity and morphology of missing tooth structure. The structural loss typically results from caries or external trauma (collectively referred to herein as cavities). Tooth structure may also be lost intentionally during tooth preparation to improve the aesthetics or the physical integrity of the intended restorative material. A direct restoration involves placing a soft or malleable filling into the prepared tooth and building up the tooth before the material sets hard. Due to their desirable aesthetic properties, resin based dental restorative materials are becoming the materials of choice by dental clinicians.

Among all different type of dental fillings, the posterior fillings are often the largest in size. In some instances, posterior fillings are also stress-bearing. Stress bearing restorations, such as those Class I and II filling at the posterior teeth, require the use of mechanically strong restorative materials to withstand the forces resulting from mastication. Such restorative materials are typically highly viscous and it is difficult and highly technique sensitive for accurate placement of the restorative materials. Posterior cavities are often deep, sometimes as deep as 7 mm or more. Currently, the vast majority of posterior dental filling materials are cured by blue light at the wavelength of around 468 nm. The effective penetration of light is often not deeper than 5 mm, rendering such techniques unsuitable for filling deeper cavities (e.g., without using more complicated and/or time consuming techniques). These materials also have shrinkage during curing, which introduce stress. The nature of curing that is initiated by light is that polymerization happens in a very fast motion, which usual result in significant stress to the tooth structure.

In some instances, it may be possible mitigate these defects and risks by filling cavities incrementally in thin layers. Each incremental layer is cured individually before placing a subsequent one to counteract polymerization stress and low light penetration depth. This method is therefore relatively time-consuming and increase risks of leaving voids between the layers, which would significantly weaken the restorations and introduce risks of failures of restorations.

Inadvertently, the cavity may be insufficiently filled and adaptation of the restorative material to the cavity walls may be incomplete, resulting in gaps between the restoration and the tooth structure, which can lead to increased sensitivity, intrusion of fluids and bacteria, and can result in continued tooth decay and premature failure of the restoration. The majority of clinical studies indicate the annual failure rates (AFR's) are between 1% and 3% with tooth colored fillings on posterior teeth.

SUMMARY OF THE INVENTION

In some instances, an ideal filling material (e.g., posterior filling material, or other filling material, such as for filling larger cavities) may be filled in bulk, rather than in increments, and cures (e.g., relatively) slowly from the bottom of a restoration to result in much less stress and voids. In certain embodiments, such a process and materials suitable for such applications are provided herein.

Provided in certain embodiments herein are dental compositions comprising a polymerizable monomer, and a hydroperoxide and/or thiourea. In some embodiments, the compositions further comprise copper (II) (e.g., as a catalyst). In certain embodiments, the dental compositions comprise a first part and a second part, the first part comprising a hydroperoxide and the second part comprising a thiourea. In certain embodiments, the first and/or second part comprises a polymerizable monomer (e.g., comprising an ethylenic group, such as described herein). In some embodiments, the first and/or second part comprises copper (II) (e.g., a copper (II) catalyst, such as a copper (II) compound described herein).

In specific embodiments, provided herein is a dental composition comprising a first part and a second part, the first part comprising: copper (II) (e.g., a copper (II) catalyst); a hydroperoxide; and a polymerizable monomer, the polymerizable monomer comprising an ethylenic group, and the second part comprising: copper (II) (e.g., a copper (II) catalyst); a thiourea; and a polymerizable monomer, the polymerizable monomer comprising an ethylenic group. In specific embodiments, the first and second parts are physically separated (e.g., until such a time as the dental composition is used to restore a cavity in a tooth).

In some embodiments, provided herein is a dental composition comprising a first and a second part, the first and second part collectively comprising: copper (II) (e.g., a copper (II) catalyst); a hydroperoxide; a polymerizable monomer, the polymerizable monomer comprising an ethylenic group; and a thiourea. In specific embodiments, the first part comprises the hydrogen peroxide, the second part comprises the thiourea, and the first and the second part are physically separated from each other (e.g., until such a time as the dental composition is used to restore a cavity in a tooth). In more specific embodiments, the first and second parts both comprise copper (II). In other specific embodiments, the second part (e.g., comprising thiourea) comprises copper (II). In more specific embodiments, the second part comprises copper (II), and the first part does not comprise copper (II). In some embodiments, the second part comprises more copper (II) than the first part (e.g., at least 2 times as much, at least 4 times as much, at least 5 times as much, or at least 10 times as much (e.g., by wt. %)).

In some embodiments, provided herein is a dental composition, a part thereof, or a resin precursor thereof comprising: a hydroperoxide; and a polymerizable monomer (e.g., the polymerizable monomer comprising an ethylenic group). In specific embodiments, provided herein is a dental composition, a part thereof, or a resin precursor thereof comprising: copper (II) (e.g., a copper (II) catalyst); a hydroperoxide; and a polymerizable monomer (e.g., the polymerizable monomer comprising an ethylenic group). Similarly, in certain embodiments, provided herein is a dental composition, a part thereof, or a resin precursor thereof comprising: copper (II) (e.g., a copper (II) catalyst); a thiourea; and a polymerizable monomer (e.g., the polymerizable monomer comprising an ethylenic group).

In some embodiments, provided herein is a dental composition (e.g., a fast curing, copper free, acid free composition) comprising a first and a second part, the first and second part collectively comprising: a hydroperoxide (e.g., the hydroperoxide being a tertiary aryl hydroperoxide (e.g., HOOCR'$_3$, wherein each R' is independently alkyl or aryl, with at least one R' being aryl (e.g., substituted or unsubstituted aryl), such as cumenehydroperoxide (e.g., wherein a first and second R' are methyl and a third R' is phenyl)); a polymerizable monomer (e.g., the polymerizable monomer comprising an ethylenic group); and a thiourea. In some embodiments, the first part comprises the hydrogen peroxide, the second part comprises the thiourea, and the first and the second parts are physically separated from each other. In specific embodiments, the hydroperoxide has a concentration in the dental composition (e.g., of the composition in its entirety (e.g., concentration–(weight of hydroperoxide/ weight of composition)*100%), or excluding the weight of any filler (e.g., concentration–(weight of hydroperoxide/ (weight of composition–weight filler))* 100%)) of about 1.5% (w/w) or more, or a concentration relative to the monomer (e.g., concentration–(weight of hydroperoxide/ weight of monomer)*100%) of about 1.5% (w/w) or more. In more specific embodiments, the hydroperoxide has a concentration in the dental composition (e.g., of the composition in its entirety, or excluding the filler) of about 2% (w/w) or more or a concentration relative to the monomer of about 2% (w/w) or more. In still specific embodiments, the hydroperoxide has a concentration in the dental composition (e.g., of the composition in its entirety, or excluding the filler) of about 2.5% (w/w) or more or a concentration relative to the monomer of about 2.5% (w/w) or more. In further or alternative embodiments, the thiourea has a concentration in the dental composition (e.g., of the composition in its entirety (e.g., concentration–(weight of thiourea/ weight of composition)*100%), or excluding the filler (e.g., concentration–(weight of thiourea/(weight of composition–weight filler))*100%)) of about 1.5% (w/w) or more or a concentration relative to the monomer (e.g., concentration–(weight of thiourea/weight of monomer)*100%) of about 1.5% (w/w) or more. In more specific embodiments, the thiourea has a concentration in the dental composition (e.g., of the composition in its entirety, or excluding the filler) of about 2% (w/w) or more or a concentration relative to the monomer of about 2% (w/w) or more. In still specific embodiments, the thiourea has a concentration in the dental composition (e.g., of the composition in its entirety, or excluding the filler) of about 2.5% (w/w) or more or a concentration relative to the monomer of about 2.5% (w/w) or more. In further or additional embodiments, the combined weight of the hydroperoxide plus thiourea has a concentration in the dental composition (e.g., of the composition in its entirety, or excluding the filler) of about 3% (w/w) or more or a concentration relative to the monomer of about 3% (w/w) or more. In more specific embodiments, the combined weight of the hydroperoxide plus thiourea has a concentration in the dental composition (e.g., of the composition in its entirety, or excluding the filler) of about 4% (w/w) or more or a concentration relative to the monomer of about 4% (w/w) or more. In still specific embodiments, the combined weight of the hydroperoxide plus thiourea has a concentration in the dental composition (e.g., of the composition in its entirety, or excluding the filler) of about 5% (w/w) or more or a concentration relative to the monomer of about 5% (w/w) or more. In certain instances, the amount of thiourea and hydroperoxide present in the composition are less than an amount that would result in the failure to cure the composition and/or failure of a restoration material resulting from the combination of the parts of and the curing of the composition. In certain embodiments, the amount of thiourea and/or hydroperoxide (individually or in combination) in the dental composition (e.g., of the composition in its entirety, or excluding the filler) is less than 50% (w/w) of monomer, less than 30% (w/w) of monomer, less than 20% (w/w) of monomer, less than 10% (w/w) of monomer, or the like.

In certain embodiments, the copper (II) or copper (II) catalyst comprises a copper (II) ion and/or a copper (II) compound (e.g., copper (II) salt, complex, or other dentally acceptable compound). In specific embodiments, the copper (II) compound or catalyst comprises copper (II) sulfate, copper (II) acetate, copper (II) chloride, copper (II) acetylacetonate, or a combination thereof. In some embodiments, the copper (II) (e.g., copper (II) compound or catalyst) is present in the composition (e.g., of the composition in its entirety, or excluding the filler) in an amount of about 5 wt. % or less (e.g., about 1 wt % or less, or about 0.1 wt. % or less). In specific embodiments, a copper (II) compound is present in the composition (e.g., of the composition in its entirety, or excluding the filler) in an amount of about 5 wt. % or less (e.g., about 1 wt % or less, or about 0.1 wt. % or less). In certain embodiments, the amount of copper (II) present in the composition is sufficient to facilitate a desired cure time (e.g., of a composition provided herein wherein the first and second parts thereof are combined), such as any desirable cure time described herein.

In some embodiments, the hydroperoxide comprises a hydrocarbon (e.g., $C_4$-$C_{20}$ hydrocarbon) substituted with one or more —OOH group. In specific embodiments, the hydroperoxide is a tertiary hydroperoxide (e.g., the —OOH group is substituted with a carbon having tertiary substitution). In more specific embodiments, the hydroperoxide is or comprises t-butyl hydroperoxide, t-amyl hydroperoxide, p-diisopropylbenzenehydroperoxide, cumenehydroperoxide, pinanehydroperoxide, p-menthanehydroperoxide, 1,1,3, 3-tetramethylbutyl hydroperoxide, or a combination thereof. In further or alternative embodiments, the hydroperoxide is present in the composition (e.g., of the composition in its entirety, or excluding the filler) in an amount of about 0.01% (w/w) to about 10% (w/w). In more specific embodiments, the hydroperoxide is present in the composition in an amount of about 0.1% (w/w) to about 6% (w/w), e.g. about 0.1% (w/w) to about 5% (w/w). In some embodiments, the hydroperoxide is present in the composition in a ratio of hydroperoxide to polymerizable monomer of about 1:9999 to about 1:9. In more specific embodiments, the ratio of hydroperoxide to polymerizable monomer is about 1:99 to about 5:95.

In certain embodiments, the monomer is a dentally acceptable monomer. In some embodiments, the monomer comprises a vinyl, an acrylate, a methacrylate (e.g., a dimethacrylate), or a combination thereof. In further or alternative embodiments, the monomer is present (e.g., by weight in the entire composition, including any filler) in an amount of about 10% (w/w) to about 60% (w/w). In more specific embodiments, the polymerizable monomer is present in an amount of about 20% (w/w) to about 50% (w/w).

In certain embodiments, the thiourea is a (hetero)arylthiourea, a (hetero)arylcarbonylthiourea, a (hetero)alkylcarbonylthiourea, a (hetero)alkylthiourea, or the like. In specific embodiments, the thiourea is or comprises 1-(2-Pyridyl)-2-thiourea (PTU), 1-Benzoyl-2-thiourea (BTU), 1-Acetyl-2-thiourea (ATU), 1-(2-Tetrahydrofurfuryl)-2-thiourea (TTU), or a combination thereof. In further or alternative embodiments, the thiourea is present in the composition in a ratio of thiourea to polymerizable monomer of about 1:999 to about 100:900. In more specific embodiments, the ratio of thiourea to polymerizable monomer is about 1:99 to about 10:90.

In specific embodiments, the hydroperoxide is cumene hydroperoxide. In further or alternative embodiments, the thiourea is 1-(2-Pyridyl)-2-thiourea (PTU). In more specific embodiments, the hydroperoxide is cumene hydroperoxide and the thiourea is 1-(2-Pyridyl)-2-thiourea (PTU). Other specific hydroperoxides and thioureas, as well as combinations thereof, are set forth in the examples. In addition, specific embodiments, specific monomers and combinations thereof as included in compositions herein are as set forth in the examples. Other specific agents and combinations of agents as set forth in the examples and included in the disclosure herein, in any combination exemplified.

In specific embodiments, a dental composition provided herein comprises a filler. In more specific embodiments, the first and second parts comprise a filler. In still more specific embodiments, the filler is a finely divided filler. In some embodiments, the finely divided filler comprises a plurality of particles. In specific embodiments, the particles having an average dimension (e.g., diameter) of about 0.02 microns to about 30 microns, e.g., about 0.2 microns to about 10 microns. In further or alternative embodiments, the filler comprises an inorganic filler, a pre-polymerized filler, or a combination thereof. Fillers include, by way of non-limiting example, metal oxide, a metal nitride, a metal fluoride, a silicate, silica (e.g., colloidal silica, precipitated silica, fused silica), an aluminosilicate, an aluminoborosilicate, a fluoroaluminosilicate, a bariumsilicate, a bariumaluminosilicate, a barium aluminoborosilicate, a strontiumaluminosilicate, a bariumfluoroaluminosilicate, a strontiumfluoroaluminosilicate, a strontiumzincfluoroaluminosilicate, a zinc aluminosilicate, a pre-polymerized filler, and a combination thereof. In some embodiments, the filler is present in an amount (e.g., of the entire composition, including all components) of about 10% (w/w) to about 90% (w/w). In more specific embodiments, the filler is present in an amount of about 40% (w/w) to about 80% (w/w). In still more specific embodiments, the filler is present in an amount of about 60% (w/w) to about 80% (w/w).

In some embodiments, the composition comprises a photoinitiator, a stabilizer, a solvent, or any combination thereof. In some embodiments, a photoinitiator is present (e.g., by weight relative to the weight of the composition in its entirety, or to the weight composition excluding the filler) in an amount of about 5% (w/w) or less. In further or alternative embodiments, a stabilizer is present (e.g., by weight relative to the weight of the composition in its entirety, or to the weight composition excluding the filler) in an amount of about 1% (w/w) or less.

In some embodiments, a composition provided herein is free of, or substantially free of, an acid or anhydride. In specific embodiments, the composition (and/or part(s) thereof) (e.g., by weight relative to the weight of the composition in its entirety, or to the weight composition excluding the filler) comprises less than 10% (w/w) of an acid and/or anhydride—alone or in combination—(e.g., less than 8% (w/w), less than 5% (w/w), less than 3% (w/w), less than 1% (w/w), or less than 0.5% (w/w)). In some embodiments, the composition and/or parts thereof are non-acidic (e.g., has a pH of about 5 or more).

In various embodiments, compositions provided herein have good performance characteristics, such as when utilized in restorative dental applications (e.g., in restoring a tooth with a Class I or Class II cavity). In specific embodiments, upon combination of the first and second parts, the total volume of the composition shrinks by less than 10% (e.g., less than 8%, less than 6%, or less than 4%) (e.g., as it sets). In some instances, minimizing such shrinkage reduces the incidences of void formation between a filling and a tooth, reduces incidences of damage (e.g., cracking) to the tooth during and following restoration, and the like. In further or alternative embodiments, upon combination of the first and second parts, the hygroscopicity of the composite is less than 100 μg/mm$^3$ (e.g., less than 50 μg/mm$^3$, less than 25 μg/mm$^3$, less than 20 μg/mm$^3$, or less than 15 μg/mm$^3$). In some instances, minimizing the hygroscopicity reduces expansion of the restoration material following curing to a resultant composite which, in turn, may reduce incidences of damage (e.g., cracking) to the tooth, dislodgement of the filling from the tooth, and/or the like.

Also provided herein are dental composites comprising resulting from the mixing of composition parts described herein, e.g., partially or wholly cured mixtures. In some embodiments, the composite comprises a partially or wholly cured resin (e.g., comprising polymer—such as polymerized monomer described herein), filler and copper. In specific embodiments, the composite comprises the cured resin in an amount of about 10% (w/w) to about 60% (w/w), the filler in an amount of about 10% (w/w) to about 90% (w/w), and the copper in an amount of about 1 elemental wt. % or less. Also provided herein is a mixture comprising copper (II) (e.g., a copper (II) catalyst); a hydroperoxide; a polymerizable monomer, the polymerizable monomer comprising an ethylenic group; and a thiourea. The reaction mixture may be partially cured, with a portion of the monomeric units thereof forming monomers and other portions forming oligomer or polymers thereof.

In some embodiments, two part compositions provided herein are contained within a dual chambered device comprising a housing body, the housing body comprising a first chamber and a second chamber, the first chamber containing the first part of a composition described herein, the second chamber containing the second part of a composition described herein. In specific embodiments, dual chambered device is configured to concomitantly extrude and/or mix the first and second parts.

Also provided herein is a method for restoring a tooth in an individual. In some embodiments, the process comprises combining a first composition (e.g., a first part of a dental composition described herein) with a second composition (e.g., a second part of a dental composition described herein) to form a mixed composition. In specific embodiments, the first composition comprising a hydroperoxide, the second composition comprising a thiourea, and one or both of the first and/or second compositions comprising copper (II) (e.g., a copper (II) catalyst), a polymerizable monomer (e.g., the polymerizable monomer comprising an ethylene group), and a filler. In some embodiments, the method further comprises administering the mixed composition to an individual (e.g., to a Class I or Class II cavity in a tooth of the individual). In some embodiments, the process further comprises curing the mixed composition (e.g., allowing the composition to self-cure, and/or using a dental curing light to photo-cure the composition). In specific embodiments, curing of the mixed composition results in the formation of a restoration composite (e.g., in the form of a filling within a dental cavity of the individual). In preferred embodiments, the curing step (e.g., self-curing) occurs relatively quickly in order to facilitate the restoration process. In specific embodiments, the curing step (e.g., self-curing or setting) occurs within 10 minutes, within 4 minutes, within 2 minutes, or the like.

In some embodiments, the method comprises removing decay from in and around a cavity to be filled (e.g., drilling the tooth to remove decay therefrom). In certain embodiments, a cavity to which the composition is to be administered is a Class I or Class II cavity. In some specific embodiments, a cavity to which the composition is to be administered has a depth of at least 3 mm, e.g., at least 4 mm, at least 5 mm, 5 mm to 7 mm, or the like.

These and other objects, features, and characteristics of the compositions, parts thereof, precursors thereof, resultant composites, and methods disclosed herein, as well as the methods of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE INVENTION

Figures 1A, 1B:
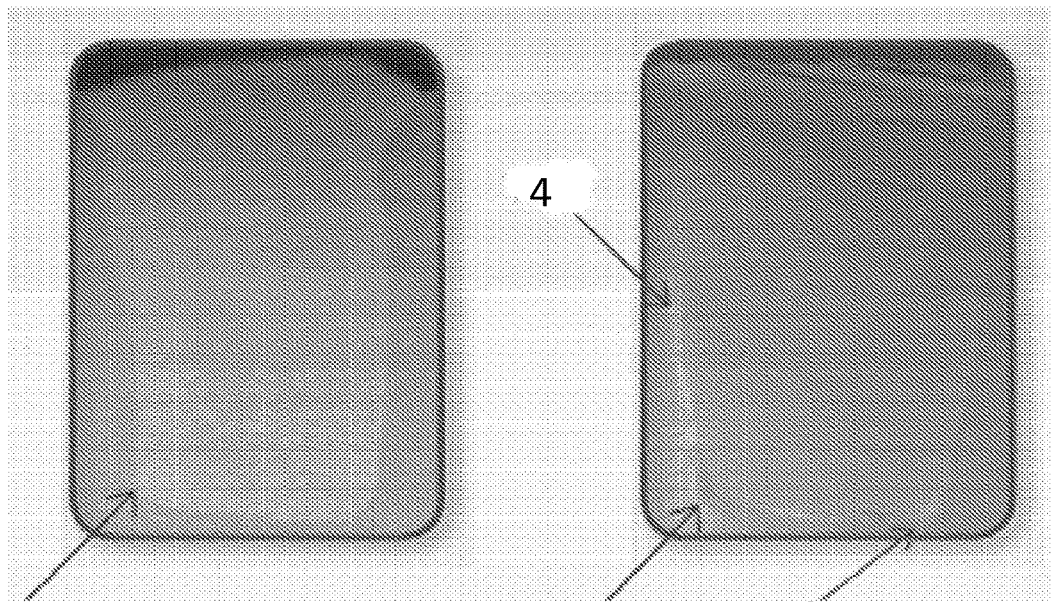
FIGS. 1A and 1B illustrates a cross-sectional image of the filling of a cavity using a composition described herein (FIG. 1A) versus a commercially available restoration composition (FIG. 1B).

Provided in certain embodiments herein are dental compositions. Also provided in certain embodiments herein are component parts thereof, dental restoration processes, resins used in the preparation of dental compositions, dental composites (e.g., filling materials), and the like. In specific embodiments, the dental compositions comprise two parts, such as two parts that are kept physically separated from each other. In some instances, when the two parts are combined, such as when the dental composition is used in a dental restoration process (such as described herein), the composition forms a composite (e.g., a filling material used in tooth restoration).

In some embodiments, provided herein is a dental composition comprising two parts (e.g., with free radical polymerization being initiated upon the mixing thereof), the two part dental composition comprising, in some embodiments: (1) at least one monomer with at least one ethylenically unsaturated group (e.g., also referred to herein as a polymerizable monomer comprising an ethylenic group, such as described herein); (2) one part comprising at least one hydroperoxide group; and (3) one part comprising at least one substituted thiourea. In more specific embodiments, the two part dental composition comprises: (1) at least one monomer with at least one ethylenically unsaturated group; (2) one part comprising at least one hydroperoxide group; (3) one part comprising at least one substituted thiourea; (4) at least one part comprising at least one copper (II) compound (e.g., a copper (II) compound that catalyzes, such as, facilitates and/or speeds up curing of the composition (e.g., polymerization of the monomeric components thereof) upon combination of the first and second parts).

In specific embodiments, provided herein is a dental composition comprising a first and a second part, the first part comprising: (1) copper (II) (e.g., a copper (II) catalyst); (2) a hydroperoxide; and (3) a polymerizable monomer comprising an ethylenic group, and the second part comprising: (1) copper (II) (e.g., a copper (II) catalyst); (2) a thiourea; and (3) a polymerizable monomer comprising an ethylenic group. Also provided herein are the individual first and second parts thereof, including, e.g., a dental composition comprising (1) copper (II) (e.g., a copper (II) catalyst); (2) a hydroperoxide; and (3) a polymerizable monomer comprising an ethylenic group, and/or a dental composition comprising (1) copper (II) (e.g., a copper (II) catalyst); (2) a thiourea; and (3) a polymerizable monomer comprising an ethylenic group. Alternatively, in some embodiments, the first part does not comprise copper (II).

In certain embodiments, provided herein is a dual chambered device comprising a housing body, the housing body comprising a first chamber and a second chamber, the first chamber containing therein the first part of a composition described herein, and the second chamber containing therein the second part of a composition provided herein. In some embodiments, the dual chambered device is any suitable device suitable for concomitantly extruding the first and second parts, such as to allow the mixing of the first and second parts and facilitate initiation and polymerization of the monomeric component(s) thereof. In specific embodiments, the dual chambered device is a dual barreled syringe comprising a nozzle configured to facilitate mixing of the first and second parts upon (concurrent) depression of a first and a second plunger (e.g., wherein the first and second plungers displace the first and second parts of the composition from the dual chambered device upon depression thereof).

Figure 3:
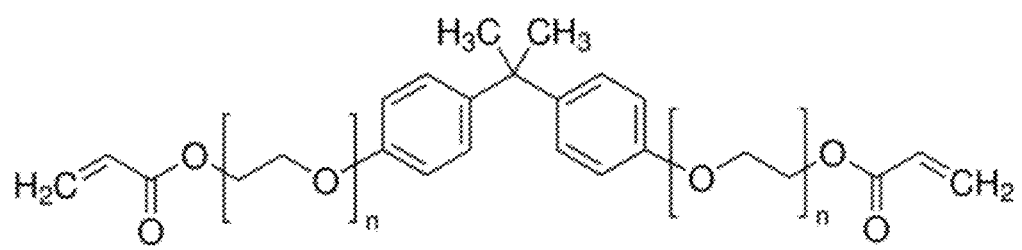
FIG. 3 illustrates an exemplary monomer used herein comprising an ethylenic group (a diacrylate).

In certain embodiments, the monomer with at least one ethylenically unsaturated group or polymerizable monomer comprising an ethylenic group is a compound comprising at least one >C=C< group. In specific embodiments, the monomer is represented by the formula $R_2C=CR_2$, wherein each R is independently selected from H, $COOR^1$, or an optionally substituted hydrocarbon, such as alkyl, aryl, or the like, such as wherein at least one R is not H. In specific embodiments, at least one R is $COOR^1$ or an aryl (e.g., phenyl, or the like). In some embodiments, $R^1$ is either H, (hetero)alkyl (e.g., $C_1$-$C_6$ alkyl) (wherein "(hetero)alkyl" refers to herein as either alkyl or heteroalkyl), (hetero)alkylaryl, aryl(hetero)alkyl, (hetero)-alkylaryl(hertero)alkyl, or the like. In more specific embodiments, the alkyl is a $C_1$-$C_6$ alkyl (e.g., methyl, ethyl, or the like). In certain embodiments, an alkyl is an acyclic (e.g., branched or straight chain) or cyclic, saturated or unsaturated alkyl. In some embodiments, optional substituents include, by way of non-limiting example, —OH, alkyl, and/or aryl. In certain embodiments, the monomer comprises one or more moiety represented by the formula $R'_2C=CR'L$, wherein each of the R' and L groups are independently as described for the R groups above. In specific embodiments, adjacent L groups combine to form any suitable group, such as —COO-(hetero)alkyl-OOC—, —COO-(hetero)alkylaryl(hetero)alkyl-OOC—, —COO-(hetero)alkylarylalkylaryl(hetero)alkyl-OOC—, (hetero)alkyl, (hetero)alkylaryl(hetero)alkyl, (hetero)alkylarylalkylaryl(hetero)alkyl, or the like. In certain embodiments, the L group(s) is substituted with any suitable group or groups, such as one or more alkyl, one or more —OH group, one or more oxo (i.e., =O) group, or the like, or a combination thereof. FIG. 3 illustrates an exemplary embodiment, such as wherein adjacent L groups combine to form a —COO-heteroalkylarylalkylarylheteroalkyl-OOC— group. In certain embodiments, a monomer comprises two or more R'$_2$C=CR'L groups, wherein the L groups are linked together (e.g., as R'$_2$C=CR'L-(LCR'=CR'$_2$)$_a$, wherein a >0, such as 1-5, e.g., 1-2), such as illustrated in Formula I:

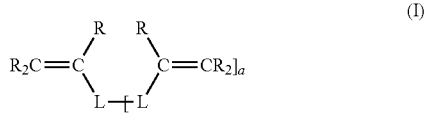

(I)

Figure 4:
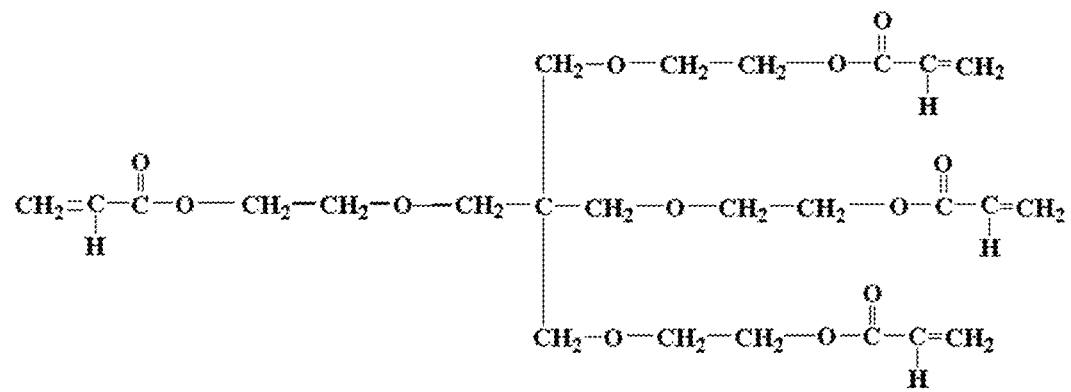
FIG. 4 illustrates an exemplary monomer used herein comprising an ethylenic group (a tetraacrylate).

For example, in some embodiments, the monomer is optionally R'$_2$C=CR'—COO((CH$_2$)$_m$(CHOH)$_n$)$_p$OOC—R'C=CR'$_2$ (e.g., wherein the L groups are each COOR, wherein the R groups, taken together and/or individually, are alkyl, optionally substituted with OH), wherein m is 1-6 (e.g., 2-4), n is 0-1, and p is 1-30 (e.g., 1-10). FIG. 4 illustrates another exemplary monomer, comprising an acrylate (the tetraacrylate, ethoxylated (4) pentaerythritoltetraacrylate), wherein each L is a —COOR' (R'=heteroalkyl group), and a=3.

In specific embodiments, the monomer is an acrylate (e.g., wherein three R groups =H and one R group =COOR$^1$), a methacrylate (e.g., wherein two R groups=H, one R group=methyl, and another R group (on the same carbon as the methyl) is COOR$^1$), or a vinyl group (wherein at least one R group is a hydrocarbon). In some embodiments, the monomer comprises an acrylate, a methacrylate, and/or a vinyl group. In specific embodiments, the ethylenically unsaturated group is selected from acrylate and methacrylate groups. Examples of polymerizable monomers include, but are not limited to, the following: glycerol di(meth)acrylate, glycerol mono(meth)acrylate, hydroxyethyl (meth)acrylate {(meth)acrylate=acrylate or methacrylate}, hydroxypropyl (meth)acrylate, methyl (meth)acrylate, ethyl (meth)acrylate, propyl (meth)acrylate, octyl (meth)acrylate, decyl (meth)acrylate, 2-ethoxyethyl (meth)acrylate, 2'-ethoxy-2-ethoxyethyl (meth)acrylate, ethyleneglycol di(meth)acrylate, diethyleneglycol di(meth)acrylate, triethyleneglycol di(meth)acrylate; polyethyleneglycol mono-(meth)acrylate, polyethyleneglycol di(meth)acrylate, polypropyleneglycol mono-(meth)acrylate, polypropyleneglycol di(meth)acrylate, polytetramethyleneglycol mono-(meth)acrylate, polytetramethyleneglycol di(meth)acrylate, hexanediol di(meth)acrylate, octanediol di(meth)acrylate, decanediol di(meth)acrylate, trimethyloylpropane tri(meth)acrylate, urethane dimethacrylate (e.g., reaction adduct of 2-hydroxyethyl methacrylate with 2,4,4-trimethylhexane diisocyanate), 2,2-bis[4-(2-hydroxy-3-methacryloylpropoxy)-phenyl]-propane (Bis-GMA), ethoxylated-bisphenol A dimethacrylate (where total number of moles of ethylene oxide in the molecule may range from 2 to 30 units, e.g., FIG. 3 illustrates ethoxylated bisphenol A dimethacrylate and n equals, for example 2-30) (e.g., ethoxylated (6) bisphenol A dimethacrylate (E6BAD) or ethoxylated (3) bisphenol A dimethacrylate (EBPADM)), tetrahydrofurfuryl (meth)acrylate, or mixtures or copolymers thereof. As referred to herein, "(meth)acrylate" includes disclosures of both methacrylate and acrylate.

In certain embodiments, the amount of monomer present in the composition is any suitable amount (e.g., to facilitate curing of the composition into a dentally acceptable restoration material). In certain embodiments, a dental composition provided herein comprises monomer in a weight percentage (e.g., of the total composition) amount between 10% and 60'%. In more specific embodiments, the weight percentage is between 20% and 50%.

In certain embodiments, compositions provided herein comprise copper (II) (e.g., a copper (II) catalyst), such as in the form of a copper (II) compound. In specific instances, copper(II) (e.g., a copper (II) compound) is utilized to catalyze curing (e.g., hardening, or otherwise setting) of the composition (e.g., accelerate or otherwise facilitate polymerization of the monomer). In specific instances, the presence of the copper (II) (e.g., compound thereof) accelerates the polymerization process when two parts of the inventive composition are mixed (e.g., whereby separated hydroperoxide and thiourea come together and facilitate initiation of polymerization, which is accelerated by the presence of the copper (II)). A copper (II) catalyst is optionally in a disassociated, associated (e.g., in the form of a copper (II) compound), or partially associated form. In various embodiments, the copper (II) compound is any suitable compound that comprises at least one copper (II) in its molecular formula. Examples of copper (II) compounds include, but are not limited to, copper (II) sulfate, copper (II) acetate, copper (II) chloride, copper (II) acetylacetonate, and combinations thereof. In specific embodiments, the copper (II) compound is copper (II) acetate. In other specific embodiments, the said copper (II) compound is copper (II) acetylacetonate. In specific embodiments, the weight percentage of the copper (II) (or compound thereof) is less than 1% (e.g., about 0.001 wt. % to 1 wt. %). In more specific embodiments, the weight percentage of the copper (II) (or compound thereof) is less than 0.1% (e.g., about 0.001 wt. % to about 0.1 wt. %). In still more specific embodiments, the copper (II) (or compound thereof) is provided in, or combined in, a composition herein in an amount of about 0.001 wt. % to about 0.05 wt. %. In specific embodiments, such weight percentages are determined relative to the overall weight of the composition, or to the overall weight of the composition minus the weight of any filler (e.g., inorganic filler).

In certain embodiments, the hydroperoxide is any suitable agent, particularly a dentally acceptable agent, such as that when combined with a thiourea provided herein initiates and/or otherwise facilitates polymerization of the monomer herein, such as at a rate suitable for dental applications, particularly restorative applications. In some embodiments, the hydroperoxide is represented by the formula HOO—R$^2$, wherein R$^2$ is any suitable organic group. In specific embodiments, R$^2$ is a hydrocarbon, such as a C$_4$-C$_{20}$ hydrocarbon (optionally substituted with any suitable groups, such as alkyl groups, aryl groups (e.g., phenyl), alkylaryl groups, additional —OOH groups, and/or the like). In some embodiments, R$^2$ is represented by the formula: —CR$^3$R$^4$R$^5$, wherein each of R$^3$, R$^4$, and R$^5$ are independently H, alkyl (cyclic and/or acyclic, and branched or straight chain), aryl (e.g., phenyl), arylalkyl (e.g., attached to the carbon at the alkyl), alkylarylalkyl, or the like, wherein such groups are optionally substituted or unsubstituted. In some embodiments, at least two of $R^3$, $R^4$, and $R^5$ are not H. In specific embodiments, the hydroperoxide is a tertiary hydroperoxide, i.e., wherein none of $R^3$, $R^4$, and $R^5$ are H. In certain instances, any one or more of $R^3$, $R^4$, and/or $R^5$ are optionally taken together with another or both of $R^3$, $R^4$, and $R^5$ to form a cyclic (mono or polycyclic) alkyl group (which is optionally substituted or unsubstituted, such as discussed herein). As discussed herein, any suitable hydroperoxide compound with at least one hydroperoxide group is optionally used. In specific embodiments, the hydroperoxide compound comprises more than one hydroperoxide group. Non-limiting examples of hydroperoxide compounds include, but are not limited to, t-butyl hydroperoxide, t-amyl, hydroperoxide, p-diisopropylbenzenehydroperoxide, cumenehydroperoxide, pinanehydroperoxide, p-methane hydroperoxide, and 1,1,3,3-tetramethylbutyl hydroperoxide.

In some embodiments, any suitable concentration of hydroperoxide is optionally utilized in the compositions and methods provided herein. In specific embodiments, the total hydroperoxide compound(s) is in the range of about 0.01% (w/w) to about 10.0% (w/w) (e.g., of the overall composition). In certain embodiments, the hydroperoxide is present in the range of about 0.1% (w/w) to about 5.0% (w/w) of the composition (e.g., overall composition). In some embodiments, the hydroperoxide is present in the composition in an amount of about 1.5% (w/w) to about 5% (w/w). In specific embodiments, such weight percentages are determined relative to the overall weight of the composition, or to the overall weight of the composition minus the weight of any filler (e.g., inorganic filler). In certain instances, hydroperoxides provided herein, such as amongst those described above, are stable under a variety of conditions and have a long shelf-life.

Any suitable thiourea is optionally utilized in a compositions described herein (e.g., in at least one part of a two-part composition described herein). In some embodiments, the thiourea is a substituted thiourea, such as a dentally acceptable thiourea. In some embodiments, the thiourea is an organic thiourea, e.g., a thiourea substituted with an organic radical (e.g., a pyridyl, acetyl, or the like). In specific embodiments, the thiourea is represented by the structure $R^6R^7NC(\!\!-\!\!S)NR^8R^9$, wherein $R^6$, $R^7$, $R^8$, and $R^9$ are independently selected from H, $COR^{10}$, heterocycloalkyl and heteroaryl (e.g., the heterocycloalkyl or heteroaryl being substituted or unsubstituted), $R^{10}$ being an alkyl, heteroalkyl (cyclic or acylic), aryl, or heteroaryl ($R^{10}$ being substituted or unsubstituted). In specific embodiments, the thiourea group is attached to the heterocycloalkyl or heteroaryl at a carbon alpha to a heteroatom of the ring. In some embodiments, at least one of or one of $R^6$, $R^7$, $R^8$, and $R^9$ is not H. In specific embodiments, the substituted thiourea is selected from the group consisting of 1-(2-Pyridyl)-2-thiourea (PTU), 1-Benzoyl-2-thiourea (BTU), 1-Acetyl-2-thiourea (ATU), 1-(2-Tetrahydrofurfuryl)-2-thiourea (TTU) and any mixture thereof (i.e., any one or more of PTU, BTU, ATU, and/or TTU).

In certain embodiments, combination of the two parts of the composition provided herein results in curing of the composition. In specific instances, combination of the two parts, particularly the hydroperoxide and the thiourea thereof, facilitates initiation of polymerization of the monomer component of the composition. In certain embodiments, inclusion of the copper (II) catalyst accelerates the curing process (e.g., polymerization of the monomer component(s)), resulting in a set time that is fast enough to be suitable for dental applications. In some instances, when the two-parts are mixed, the mixed composition cures (e.g., sets or hardens). In one embodiment, the setting time is less than 20 minutes (e.g., without the need for photo-curing using a photo-curing device emitting a majority of light having a wavelength in the blue range (e.g., 400 nm to 530 nm, such as about 470 nm)). In one embodiment, the setting time is less than 10 minutes. In one embodiment, the setting time is less than 5 minutes. In more preferred embodiments, the cure (e.g., set) time is about 250 seconds or less. In preferred embodiments, the cure (e.g., set) time is about 180 seconds or less. In further or alternative embodiments, the composition, when the two parts are combined, has a work time of about 200 seconds or less, e.g., about 150 seconds or less. Further, in some embodiments, the work time is at least 30 seconds (e.g., to allow restoration or filling of a tooth cavity, particularly a Class I or Class II cavity).

In certain embodiments, additional additives are included in the composition and/or parts thereof. In some embodiments, any suitable additive is optionally included, such as, by way of non-limiting example, a photo-initiator, a filler, a stabilizer, a solvent, or a combination thereof. In specific embodiments, a dental composition (or part thereof) comprises a resin composition and a filler (e.g., the resin composition comprising the materials of a dental composition described herein). In more specific embodiments, each part of a composition provided herein comprises a resin composition (e.g., a composition comprising monomer described herein) and filler. In specific embodiments, agents and additives utilized in the compositions and composites provided herein are generally dentally acceptable (e.g., having sufficiently low toxicity and performing their intended purpose under intraoral conditions).

In specific embodiments, a composition (or part thereof) provided herein comprises a filler, e.g., at least one finely divided filler. In some instances, a filler may reduce polarization shrinkage, improve mechanical properties and increase radiopacity of a dental composite. In further or alternative instances, a filler may change the rheological properties of a dental composition. Exemplary fillers include, but are not limited to, metal oxides, metal nitrides, metal fluorides, silicate glass, colloidal silica, precipitated silica, fused silica, aluminosilicate glass, aluminoborosilicate glass, fluoroaluminosilicate glass, bariumsilicate, bariumaluminosilicate, bariumaluminoborosilicate, strontiumraluminosilicate, bariumnfluoroaluminosilicate, strontiumfluoroaluminosilicate, strontiumzincfluoroaluminosilicate, zincaluminosilicate pre-polymerized composite filler, and any combination of one or more thereof. Examples of metal oxides and fluorides include, but are not limited to, barium oxide, strontium fluoride, barium fluoride, ytterbium fluoride, yttrium fluoride, zinc oxide, bismuth (III) oxide. In one embodiment, the said filler is treated with a coupling agent such as γ-methacryloyloxypropyltrimethoxysilane (MPTMS). In some instances, such treatment enhances the interfacial bonding between the filler and resin matrix, and improves mechanical properties.

In some embodiments, the filler is a finely divided filler, e.g., a filler comprising or comprised of a plurality of solid particles. In certain embodiments, the finely divided filler (e.g., particles thereof) has any suitable average dimension, such as, for example, an average size (e.g., particle size) of between 0.02 micron (μm) and 30 micron. In specific embodiments, the average size is between 0.2 micron and 10 micron.

In certain embodiments, the filler is present in a composition provided herein in any suitable amount. In some embodiments, the filler (e.g., finely divided filler) is present in the composition in an amount between 10 wt. % and 90 wt. %. In specific embodiments, the weight percentage is between 40% and 80%.

In certain embodiments, a composition (or part thereof) provided herein further comprises at least one photo-initiator. Any suitable photo-initiator(s) is optionally included. Examples of a photo-initiator include, but are not limited to, benzoin and derivatives, 2,2-diethoxy acetophenone, camphoroquinone, 1-phenyl-1,2-propanedione, monoacylphosphine oxide, bisacylphosphine oxide, and a mixture thereof. Additionally, an activator can be used together with a photo-initiator. Examples of activators include, but are not limited to, 2-ethyl-4-(N,N-dimethylamino) benzoate, 2-amyl-4-(N,N-dimethylamino) benzoate, 2-octyl-4-(N,N-dimethylamino) benzoate; 2-(ethylhexyl)-4-(N,N-dimethylamino) benzoate, N,N-dimethylaminoethyl methacrylate, N,N-dimethylaminophenethyl alcohol and a mixture thereof. In one embodiment, the photo-initiator system comprises camphoroquinone and a tertiary amine selected from the group of 2-ethyl-4-(N,N-dimethylamino) benzoate, 2-amyl-4-(N,N-dimethylamino) benzoate, 2-octyl-4-(N,N-dimethylamino) benzoate; 2-(ethylhexyl)-4-(N,N-dimethylamino) benzoate, N,N-dimethylaminoethyl methacrylate, N,N-dimethylaminophenethyl alcohol and any mixture of one or more thereof. In one embodiment, the weight percentage of the photo initiator is less than 5%. In one embodiment, the weight percentage of the photo initiator is less than 3%. In specific embodiments, such weight percentages are determined relative to the overall weight of the composition, or to the overall weight of the composition minus the weight of any filler (e.g., inorganic filler).

In certain embodiments, a composition provided herein comprises at least one stabilizer. In some instances, a stabilizer is an agent that inhibits polymerization, such as of the monomer component(s) of a composition described herein. In certain instances, such agents are useful for improving the shelf life of a composition provided herein (e.g., inhibiting polymerization of the monomer prior to use). Any suitable stabilizer, or polymerization inhibitor (such as a free radical scavenger), is optionally utilized herein. Stabilizers include, by way of non-limiting example, 2,6-di-(tert-butyl)-4-methylphenol (BHT) and 4-methoxyphenol (MEHQ). Any suitable amount of stabilizers is optionally utilized, such as less than 1 wt. %. In specific embodiments, such weight percentages are determined relative to the overall weight of the composition, or to the overall weight of the composition minus the weight of any filler (e.g., inorganic filler).

In various embodiments, the first and/or second parts provided herein are optionally provided in any suitable ratio, such as to provide an overall composition having the characteristics provided herein. In certain embodiments, the ratio of the first part to the second part (e.g., present in a composition herein and/or provided in a process herein) is about 99:1 to about 1:99. In some embodiments, the ratio of the first part to the second part is about 9:1 to about 1:9. In specific embodiments, the ratio of the first part to the second part is about 4:1 to about 1:4 or about 2:1 to about 1:2. In more specific embodiments, the ratio of the first part to the second part is about 1:1.

In certain embodiments, provided herein are methods of utilizing and manufacturing such compositions, such as in and for dental applications. In general instances, such compositions are prepared in a dentally acceptable manner (i.e., in a manner suitable for administration into the mouth (or tooth cavity thereof) of an individual, patient or person). In specific embodiments, provided herein is a method of administering a composition described herein to an individual, such as to restore a tooth of the individual. In specific embodiments, a composition described herein is provided, any parts thereof are combined to form a mixed composition (e.g., wherein the monomers of the compositions are being polymerized), administering the mixed composition to the individual (e.g., into a cavity of the individual), and curing the mixed composition (e.g., until set).

In specific embodiments, the method is utilized to restore a tooth (e.g., a tooth comprising a cavity). In some embodiments, the composition is administered to, delivered into, and/or used to restore a tooth comprising a Class I or Class II cavity (e.g., based on the G.V. Black classification system), or a cavity in a posterior tooth. In certain embodiments, a Class I cavity is a cavity located in a pit or fissure of the occlusal surfaces of molars and premolars, the occlusal two-thirds of the buccal surfaces of molars, the lingual surfaces of upper incisors, or in the lingual surfaces of upper molars. In some embodiments, a Class II cavity is a cavity in the proximal surface of a molar or premolar. In certain embodiments, the composition is particularly useful in providing an effective mechanism of filling large cavities—an area where other restoration compositions are lacking. In specific embodiments, a cavity treated according to a process herein has a depth of about 3 mm or more (e.g., about 4 mm or more, about 5 mm or more, about 5 mm to about 7 mm, or the like) from any surface of the tooth (e.g., the fill surface of the tooth, or where the surface of the tooth was prior to the cavity, or would have been in the absence of the cavity).

In specific instances, two parts of the composition are mixed and mixture is then delivered into a Class I or Class II cavity (or any other cavity type described herein). Upon waiting for a certain period of time, the mixture eventually sets. In one embodiment, the setting time is between 1 min and 5 min (e.g., at intra oral conditions (e.g., within the mouth of an individual to whom the composition is administered)). In one embodiment, the setting time is between 0.2 min and 5 min (e.g., at intra oral conditions). In one embodiment, the setting time is between 0.5 min and 3 min (e.g., at intra oral conditions).

In some embodiments, the mixture is further cured by a dental curing light, e.g., after it sets at the intraoral conditions. In further or alternative embodiments, an additional layer of a dental composition provided herein is placed on top of the set or cured mixture followed by curing with a dental curing light.

In specific embodiments, the parts of a composition provided herein are mixed (e.g., passively combined, such as put into contact with each other, or actively integrated) to form a mixed composition, the mixed composition being administered to an individual (e.g., a dental cavity of the individual), and the mixed composition being cured under ambient (e.g., intraoral) conditions (or, being allowed to self-cure) for up to 5 minutes (e.g., 0.2 minutes to 5 minutes, 30 seconds to 250 seconds, or 0.5 minutes to 3 minutes). In alternative embodiments, a first or second part is administered, and the other of the first or second part is subsequently administered (e.g., thereby mixing the two parts, such as in a tooth cavity of an individual), followed by curing, such as described herein. In specific instances, curing under ambient conditions comprises allowing the composition to set (e.g., cure in the absence of a light initiator device, such as a device that emits light, a majority of which having a blue wavelength (e.g., in the 400-530 nm range, or about 470 nm)). In specific embodiments, the cured (e.g., self-cured or set) composite is further cured using a light initiator device, such as a device that emits light, a majority of which having a blue wavelength (e.g., in the 400-530 nm range, or about 470 nm). In more specific embodiments, prior to light curing, additional mixed composition is administered to the cavity. In some instances, light curing at the surface is desirable, to facilitate complete curing of the filling at the surface (e.g., wherein radical—e.g., of living polymer and/or initiator—groups may interact and die, such as a result of chemically reacting with agents in the in the ambient environment (e.g., air), such as water, prior to complete polymerization/curing).

In some embodiments, one or more of the desirable restorative material characteristics described herein is achieved in any suitable manner, such as by using the concentrations of materials described herein. In certain embodiments, provided herein is a composition (e.g., two part composition) comprising copper (II), such as described herein. In some embodiments, presence of the copper (II) catalyzes the curing (e.g., self-curing) of a composition at a rate sufficient to be dentally effective (e.g., longer cure times may reduce proper usage of the product, potentially resulting in increased failure rates of the restoration materials). In some embodiments, the amount of copper (II) (or compound thereof) present need not be much to have an effect. For example, in some embodiments, less than 0.1 wt. % or even less than 0.01 wt. % of copper (II) (or compound thereof) is utilized. In further or alternative embodiments, good curing rates are achieved using higher concentrations of hydroperoxide and/or thiourea (e.g., but not so much as to cause excessive temperatures and/or defects in the cured restoration material). In some embodiments, a composition provided herein comprises a combined concentration of hydroperoxide and thiourea (e.g., the hydroperoxide and thiourea provided in separate parts of the composition) is about 2.5 wt. % (relative to the total weight of the monomer—i.e., {{wt. hydroperoxide+wt. thiourea}/total wt monomer}*100%) or more, about 3 wt. % or more, about 4 wt. % or more, or about 5 wt. % or more (e.g., up to about 50 wt. %, up to about 30 wt. %, up to about 20 wt. %, up to about 10 wt. %, up to about 8 wt. %, or the like).

Provided in certain embodiments herein is a dental composite (e.g., a restoration material described herein) comprising the cured combination of the first and second parts of any composition herein, or the cured combination of any composition comprising thiourea with any composition comprising a hydroperoxide described herein. In certain embodiments, one or both parts of a composition described herein comprise a copper (II) catalyst. In some embodiments, a composite provided herein comprises a cured resin (e.g., comprising polymerized monomer(s) described herein), filler and copper (e.g., in any oxidation state, such as the oxidation state of the copper (II) catalyst). In specific embodiments, the composite comprises cured resin in any suitable amount, such as an amount described herein for a composition comprising a monomer (e.g., about 10 wt. % to about 60 wt. %), the filler in any suitable amount, such as an amount described herein for a composition comprising the filler (e.g., about 10 wt. % to about 90 wt. %, and the copper in an amount of about 1 elemental wt. % or less (e.g., based on amount of copper present on an elemental basis) (e.g., about 0.1 wt. % or less, about 0.05 wt. % or less, or the like). In specific embodiments, the dental composite comprises filler in an amount of about 60% (w/w) to about 80% (w/w) and cured resin in an amount of about 20% (w/w) to about 40% (w/w). In specific embodiments, such weight percentages are determined relative to the overall weight of the composite, or to the overall weight of the composite minus the weight of any filler (e.g., inorganic filler). In specific embodiments, the dental composite is a restoration material (e.g., affixed to and/or adhered to a tooth cavity, or capable of suitable therefor), such as having a thickness of greater than 3 mm, greater than 4 mm, greater than 5 mm, about 5 mm to about 7 mm, or the like.

Figures 2A, 2B:
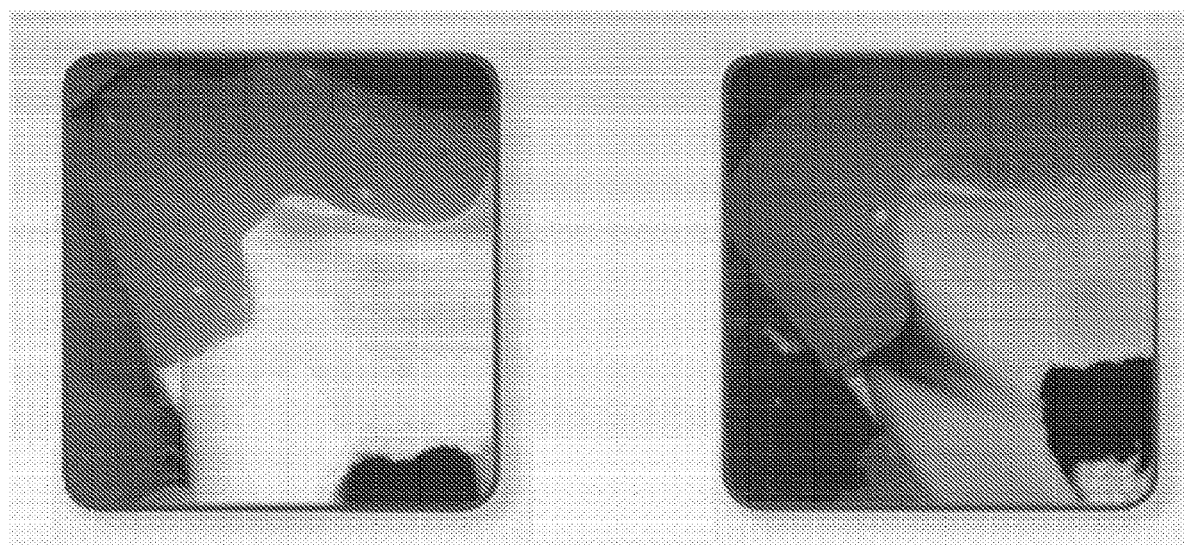
FIGS. 2A and 2B illustrates an image demonstrating the lack of microleakage observed when filling a cavity using a composition described herein (FIG. 2A) versus the microleakage observed when filling a cavity using a commercially available restoration composition (FIG. 2B).

In certain embodiments, compositions and methods provided herein are useful for restoring teeth, wherein the restoration material has good set/cure times, good adhesion, low shrinkage during curing (e.g., which, in some instances, causes voids between the filling and the tooth, leading to leakage of fluid and/or bacteria), little leakage after curing, little expansion after curing (e.g., which, in some instances, causes cracking or other distortion of the filling and/or tooth), and/or low or reduced failure rates. FIG. 1 illustrates a cross-sectional image of the filling of a cavity using a composition described herein (FIG. 1A, left) versus a commercially available restoration composition (FIG. 1B, right). As illustrated on the FIG. 1A, left, exemplary restoration materials prepared according to the processes herein and/or using the compositions provided herein provide good filling of the cavities. As indicated at the arrow 2 of the left panel of FIG. 1A, the composite material shows good adhesion and good volume retention (low shrinkage) (e.g., in cavities having depths of greater than 5 mm, such as about 7 mm). By contrast, as illustrated in the right panel of FIG. 1B (at the arrows 4), other commercial materials show poor adhesion to the cavity substrate, with voids forming 4 between the composite and the cavity substrate (e.g., in cavities having depths of greater than 5 mm, such as about 7 mm). FIG. 2 illustrates an image demonstrating the lack of microleakage observed when filling a cavity using an exemplary composition (after curing) described herein (FIG. 2A, left) versus the microleakage observed when filling a cavity using a commercially available restoration composition (after curing) (FIG. 2B, right).

In some embodiments, compositions provided and used herein demonstrate little shrinkage during curing. In certain instances, minimal shrinkage is desirable so as to avoid poor matching of a filling with a tooth, such as allowing voids to form between the filling and the tooth, such voids potentially leading to leakage of fluid and/or bacteria, which may further lead to tooth decay. In some embodiments, upon curing of a composition herein, shrinkage is about 10% or less (e.g., about 8% or less). In more specific embodiments, the shrinkage is about 6% or less, about 5% or less, about 4% or less, about 3% or less, about 2% or less, about 1% or less, or the like.

In certain embodiments, compositions provided and used herein have no to low acid and/or anhydride content. In specific embodiments, the acid and/or anhydride content is less than 5 wt. % of the composition. In more specific embodiments, the acid and/or anhydride content is less than 3 wt. % of the composition, less than 2 wt. % of the composition, less than 1 wt. % of the composition, less than 0.5 wt. %, less than 0.1 wt. % of the composition, or the like. In specific embodiments, such weight percentages are determined relative to the overall weight of the composition, or to the overall weight of the composition minus the weight of any filler (e.g., inorganic filler). In some embodiments, the composition has a substantially neutral or alkaline nature, such as a pH of about 5 or higher, a pH of about 5.5 of higher, a pH of about 6 or higher, a pH of about 6.5 or higher, or a pH of about 7 or higher. In specific instances, it is preferred that the acid content of the composition be minimized for any reason, such as to minimize hygroscopicity or water sorption of the resultant composite. In some instances, high levels of water sorption into the composite, when used as a restoration material, may result in volume expansion in the restoration material, which may lead to deformation of the restoration material, and, ultimately, dislodgement of the restoration material, damage to the tooth, and/or other undesirable outcomes.

In certain embodiments, a composition provided herein cures to a composite (or a composite provided herein has) a water sorption of about 100 µg/mm$^3$ or less. In specific embodiments, the water sorption is about 50 µg/mm$^3$ or less, about 25 µg/mm$^3$ or less, about 20 µg/mm$^3$ or less, or about 15 µg/mm$^3$.

In some embodiments, composites described herein (e.g., formed from the combination of the composition parts described herein) have good physical parameters for dental applications. In some embodiments, such composites have good flexural strength (e.g., greater than 50 MPa, greater than 100 MPa, greater than 125 MPa, or the like). In further or alternative embodiments, the composites have good compression strength (e.g., greater than 100 MPa, greater than 150 MPa, greater than 200 MPa, greater than 250 MPa, or the like). In certain embodiments, the composites have good diametral strength (e.g., greater than 30 MPa, greater than 40 MPa, greater than 45 MPa, or the like). In some embodiments, composites provided herein good water solubility (e.g., less than 1 µg/mm$^3$). In certain embodiments, the composites provided herein have good radiopacity (e.g., greater than 200% Al, greater than 300% Al, or the like). Any suitable process is optionally utilized to determine such parameters, such as testing a film comprising such a composite (e.g., the film having a thickness of about 10 microns to about 15 microns, such as about 14 microns).

Also provided herein are methods of manufacturing the compositions described herein. In some embodiments, the component parts of the compositions described herein are combined in any suitable order. Exemplary processes are set forth in the Examples. In specific embodiments, a part of a composition provided herein is prepared by combining monomer, hydroperoxide, optional stabilizer, and optional photoinitiator. In some embodiments, combination thereof is mixed to form a resin to which filler is added and blended or milled. Likewise, a part of a composition provided herein is, in specific embodiments, prepared by combining monomer, thiourea, optional stabilizer, and optional photoinitiator. In some embodiments, combination thereof is mixed to form a resin to which filler is added and blended or milled. Exemplification of specific agents (as well as the corresponding component class type) as set forth in the examples are to be understood as being included in the disclosure of compositions and methods described herein.

In some instances, as used herein, a "set time" is the amount of time under which a mixed composition provided herein (i.e., a composition combining both parts of a two-part described composition described herein) forms a solid or hard composite (which is partially or completely cured), particularly in the absence of an ancillary device designed to facilitate the curing of restoration materials, such as a dental curing light (e.g., also referred to herein as "self-curing"). A dental curing light is a piece of dental equipment that is used for polymerization of light cure resin based composites. It can be used on several different dental materials that are curable by light. The light used falls under the visible blue light spectrum. This light is delivered over a range of wavelengths and varies for each type of device. There are four basic types of dental curing lights; Tungsten halogen, light-emitting diode (LED), plasma arc curing (PAC), and laser. In certain instances, the "work time" is the length of time after which the mixed composition ceases being malleable using typical dental techniques and/or equipment.

As used herein, weight percentage (wt. % or % (w/w)) refers, unless otherwise noted, the percentage of the weight of a component relative to the overall weight of a composition or composite. In the case of non-monomer and non-filler components, the disclosure of a weight percentage (wt. % or % (w/w) also includes a disclosure of a percentage of the weight of a component relative to the overall weight of a composition or composite minus the weight of any filler (e.g., inorganic filler) in the composition or composite, whether considered as a whole, a one part system, a two part system, or the like. In some embodiments, the weight percentage refers to the weight of the component relative to the weight of a two part composition (e.g., wherein a first and second part are physically separated) and/or the weight of the component relative to the weight of one part of a two part composition. In some instances, the weight percentage of the component may be identical or similar in both parts of the two part system, and in other instances, the component may have different weight percentages in each part of the two part system. For example, in general instances, the hydroperoxide and thiourea each have different weight percentages in each of the parts, with the hydroperoxide being wholly or primarily in a first part of the composition and the thiourea being wholly or primarily in a second part of the composition.

The term "alkyl" as used herein, alone or in combination, refers to an optionally substituted straight-chain, or optionally substituted branched-chain saturated or unsaturated hydrocarbon monoradical having, e.g., from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl," means that in some embodiments, the alkyl group consists of 1 carbon atom; in some embodiments, 2 carbon atoms; in some embodiments, 3 carbon atoms; in some embodiments, 4 carbon atoms; in some embodiments, 5 carbon atoms; or, in some embodiments, 6 carbon atoms, although the present definition also covers the occurrence of the term "alkyl" where no numerical range is designated. In addition, in some instances, such as wherein the alkyl is substituted on either side (e.g., as set forth for L above), the alkyl may refer to a diradical derived from the above-defined monoradical, alkyl. Examples include, but are not limited to methylene (—CH$_2$—), ethylene (—CH$_2$CH$_2$—), propylene (—CH$_2$CH$_2$CH—), isopropylene (—CH(CH$_3$)CH$_2$—) and the like. An "alkyl" may also refer to a cyclic alkyl group, referring to an optionally substituted, saturated, hydrocarbon monoradical ring, containing, e.g., from three to about fifteen ring carbon atoms or from three to about ten ring carbon atoms, though, in some embodiments, includes additional, non-ring carbon atoms as substituents (e.g. methylcyclopropyl). The term includes fused, non-fused, bridged and spiro radicals. In some embodiments, a fused cycloalkyl contains from two to four fused rings where the ring of attachment is a cycloalkyl ring. Examples include, but are not limited to cyclopropyl, cyclopentyl, cyclohexyl, cumene, and pinane ring systems.

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings are alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, and sulfur, but not limited to these atoms and with the proviso that the ring of said group does not contain two adjacent O or S atoms. In embodiments in which two or more heteroatoms are present in the ring, the two or more heteroatoms are the same as each another, or some or all of the two or more heteroatoms are different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. In certain instances, bonding to a heteroaryl group is via a carbon atom or a heteroatom. A non-limiting example of a single ring heteroaryl group includes pyridyl or furanyl.

The term "heteroalkyl" as used herein, refers to optionally substituted alkyl structure, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, or combinations thereof). Exemplary heteroalkyl groups include straight chain groups, such as ethylene oxides (e.g., —CH2CH2On-), or ringed groups, such as tetrahydrofuran.

EXAMPLES

Abbreviations for certain materials used in certain embodiments provided herein, such as in the illustrative, non-limiting examples provided below include, as follows:
PTU: 1-(2-Pyridyl)-2-thiourea
BTU: 1-Benzoyl-2-thiourea
ATU: 1-Acetyl-2-thiourea
TTU: 1-(2-Tetrahydrofurfuryl)-2-thiourea
CHP: Cumene hydroperoxide
THPO: tert-Butyl hydroperoxide
Cu(acac)2: Copper(II) acetylacetonate
CuAc: Copper(II) acetate
GPDM: Glycerol Dimethacrylate
MDP: 12-Methacryloyldodeylphosphate
Saccharin: o-Benzoic sulfimide
R202: AEROSIL® fumed silica
R812S: AEROSIL® fumed silica
GM27884-K6: Schott GM27884 Dental Glass, 3 μm
GM39923-706: Schott GM39923 Dental Glass, 0.7 μm
Ba-Glass-15-23: Barium Dental Glass, 15 μm
YbF3: Ytterbium Fluoride
BYK W9010: Wetting and dispersing additive (flow modifier)
CQ: Camphorquinone
SR494: Ethoxylated (4) pentaerythritoltetraacrylate
EDMAB: Ethyl-4-dimethylamino benzoate
UDMA: Urethane dimethacrylate
E6BAD: Ethoxylated (6) Bisphenol A Dimethacrylate
EBPADM: Ethoxylated (3) Bisphenol A Dimethacrylate
BisGMA: Bisphenol A-glycidyl methacrylate
TEGDM: Triethylene glycol dimethacrylate
BHT: Butylatedhydroxytoluene

Example 1

A paste of $Cu(acac)_2$ is made into the composition listed in Table 1. All components are mixed and milled using a three-roll mill.

TABLE 1

| (in parts) | Ex. 1A | Ex. 1B |
|---|---|---|
| EBPADM | 89.5 | 89.5 |
| Cu(acac)2 | 0.5 | |
| CuAc | | 0.5 |
| R202 | 10.00 | 10.00 |

Examples 2 to 19

Resins containing hydroperoxides are made into the compositions listed in Table 2. All components are mechanically mixed or magnetically stirred to form homogeneous mixtures or solutions.

TABLE 2

| (in parts) | Ex. 2R | Ex. 3R | Ex. 4R | E. 5R | Ex. 6R | Ex. 7R |
|---|---|---|---|---|---|---|
| BisGMA-TEGDM | 28.2 | 28.2 | 39.0 | 39.0 | 39.0 | 18.7 |
| TEGDM | 10.8 | 10.8 | 10.0 | 10.0 | 10.0 | 12.0 |
| UDMA | 13 | 13 | 5.0 | 5.0 | 5.0 | 21.0 |
| EBPADM | 45.5 | 45.5 | 36.0 | 35.0 | 35.0 | 45.0 |
| SR494 | — | — | 7.0 | 7.0 | 7.0 | — |
| EDMAB | — | — | 0.4 | 0.4 | 0.4 | — |
| CQ | — | — | 0.2 | 0.2 | 0.2 | — |
| BYK W9010 | 0.2 | 0.2 | 0.3 | 0.3 | 0.3 | — |
| BHT | 0.1 | 0.1 | 0.1 | 0.1 | 0.1 | 0.1 |
| CHP | — | 1.1 | 2.5 | 3.0 | — | 3.0 |
| THPO | 2.2 | 1.1 | — | — | 3.0 | — |

The resin examples (resin examples denoted with an "R") above (Table 2) are used to prepare the following paste compositions listed in Table 3. All components are mixed and dispersed with the aid of a 3-roll mill.

TABLE 3

| (in parts) | Ex. 2 | Ex. 3 | Ex. 4 | Ex. 5 | Ex. 6 | Ex. 7 |
|---|---|---|---|---|---|---|
| Resin | 31.7 (Ex. 2R) | 31.7 (Ex. 3R) | 33.2 (Ex. 4R) | 33.2 (Ex. 5R) | 31.7 (Ex. 6R) | 37.85 (Ex. 7R) |
| GM27884-K6 | 63.6 | 63.6 | 61.1 | 61.6 | 63.3 | — |
| GM39923-706 | — | — | — | — | — | 62.0 |
| YbF3 | 4.5 | 4.5 | 4.7 | 4.7 | 4.5 | — |
| R202 | 0.45 | 0.45 | 1.0 | 0.47 | 0.45 | — |
| R812S | — | — | — | — | — | 0.15 |

Resins containing thiourea compounds are made into the compositions listed in Table 4. All components are mechanically mixed or magnetically stirred to form homogeneous mixtures or solutions.

TABLE 4

| (in parts) | Ex. 8R | Ex. 9R | Ex. 10R |
|---|---|---|---|
| BisGMA-TEGDM | 26.0 | 39.0 | 19.1 |
| TEGDM | 10.0 | 10.0 | 12.0 |
| UDMA | 12.0 | 5.0 | 20.0 |
| EBPADM | 42.0 | 36.0 | 45.5 |
| SR494 | 7.0 | 7.0 | — |
| EDMAB | 0.5 | 0.4 | 1.0 |
| CQ | 0.2 | 0.2 | 0.15 |
| BYK W9010 | 0.2 | 0.3 | — |
| BHT | 0.05 | 0.1 | — |
| PTU | 2.0 | 2.0 | — |
| ATU | — | — | 2.0 |

The resin examples above are used to prepare the following paste compositions listed in Table 5. All components are mixed and dispersed with the aid of a 3-roll mill.

TABLE 5

| (in parts) | Ex. 8 | Ex. 9 | Ex. 10 | Ex. 11 | Ex. 12 | Ex. 13 |
|---|---|---|---|---|---|---|
| Resin | 31.7 (Ex8R) | 33.2 (Ex9R) | 32.2 (Ex 9R) | 32.6 (Ex 9R) | 32.6 (Example 9R) | 36.9 (Ex 10R) |
| GM27884-K6 | 63.3 | 61.1 | 60.0 | 60.5 | 60.5 | — |
| Ba-Glass-15-23 | — | — | — | — | — | 61.0 |
| YbF3 | 4.5 | 4.7 | 4.6 | 4.7 | 4.7 | — |
| R202 | 0.45 | 1.0 | 0.46 | 0.47 | 0.47 | — |
| R812S | — | — | — | — | — | 0.15 |
| Ex. 1A | — | — | 2.8 | 1.9 | — | 1.0 |
| Ex. 1B | — | — | — | — | 1.9 | — |

The two-part paste examples containing either a chemical reductant (thiourea) or oxidant (hydroperoxide) compound above are combined (e.g., in about a 1:1 ratio) to measure the resultant work/set times for their respective initiator systems. Work/set times are determined under ambient conditions (e.g., at 22° C., without a dental cure light), with exemplary work/set times illustrated in Table 6.

TABLE 6

| Ex. | Combine Exs. | Thiourea wt. % in part A | Hydroperoxide wt. % in part B | Catalyst wt. % in part A | Work/Set Time (seconds) |
|---|---|---|---|---|---|
| 11a | 2 + 8 | PTU (2%) | THPO (2.2%) | — | >600 |
| 12a | 3 + 8 | PTU (2%) | 1.1% THPO & CHP | — | 360/510 |
| 13a | 4 + 9 | PTU (2%) | CHP (2.50%) | — | 120/140 |
| 14 | 5 + 9 | PTU (2%) | CHP (3.0%) | — | 105/130 |
| 15 | 5 + 10 | PTU (2%) | CHP (3.0%) | 3% Ex. 1A | 45/65 |
| 16 | 5 + 11 | PTU (2%) | CHP (3.0%) | 2% Ex. 1A | 60/80 |
| 17 | 5 + 12 | PTU (2%) | CHP (3.0%) | 2% Ex. 1B | 65/80 |
| 18 | 6 + 11 | PTU (2%) | THPO (3.0%) | 2% Ex. 1A | 240/275 |
| 19 | 7 + 13 | ATU (2%) | CHP (3.0%) | 1% Ex. 1A | 180/210 |

As is illustrated in Table 6, faster work/set times are achieved for compositions comprising copper (II), even at very low concentrations, compared to otherwise similar compositions lacking copper (II).

Examples 20 to 26

Resins containing hydroperoxides are made into a composition listed in Table 7. All components are mechanically mixed or magnetically stirred to form homogeneous mixtures or solutions.

TABLE 7

| (in parts) | Ex. 20R |
|---|---|
| E6BAD | 20.0 |
| BisGMA-TEGDM | 15.0 |
| TEGDM | 18.0 |
| UDMA | 9.0 |
| EBPADM | 34.15 |
| EDMAB | 0.40 |
| CQ | 0.20 |
| BYK W9010 | 0.80 |
| BHT | 0.10 |
| CHP | 2.85 |

The resin examples above were used to prepare the following paste compositions listed in Table 8. All components were mixed and dispersed with the aid of a 3-roll mill.

TABLE 8

| (in parts) | Ex. 20 |
|---|---|
| Resin | 29.0 (Ex. 20R) |
| GM27884-K6 | 60.49 |
| YbF3 | 9.0 |
| R812S | 1.50 |

Resins containing thiourea compounds are made into the compositions listed in Table 9. All components are mechanically mixed or magnetically stirred to form homogeneous mixtures or solutions.

TABLE 9

| (in parts) | Ex. 21R | Ex. 22R | Ex. 23R |
|---|---|---|---|
| E6BAD | 22.0 | 22.0 | 22.0 |
| BisGMA-TEGDM | 16.50 | 16.50 | 16.50 |
| TEGDM | 19.80 | 19.80 | 19.80 |
| UDMA | 9.90 | 9.90 | 9.90 |
| EBPADM | 28.88 | 28.88 | 28.88 |
| EDMAB | 0.44 | 0.44 | 0.44 |
| CQ | 0.22 | 0.22 | 0.22 |
| BYK W9010 | 0.33 | 0.33 | 0.33 |
| BHT | 0.11 | 0.11 | 0.11 |
| BTU | 1.82 | — | — |
| TTU | — | 1.82 | — |
| PTU | — | — | 1.82 |

The resin examples above are used to prepare the following paste compositions listed in Table 10. All components are mixed and dispersed with the aid of a 3-roll mill.

TABLE 10

| (in parts) | Ex. 21 | Ex. 22 | Ex. 23 |
|---|---|---|---|
| Resin | 26.0 (Ex. 21R) | 26.0 (Ex. 22R) | 26.0 (Ex. 23R) |
| GM27884-K6 | 60.3 | 60.3 | 60.3 |
| YbF3 | 9.0 | 9.0 | 9.0 |
| R812S | 1.50 | 1.50 | 1.50 |
| Ex. 1A | 3.0 | 3.0 | 3.0 |

The two-part paste examples containing either a chemical reductant or oxidant compound above are combined (e.g., in about a 11 ratio) to measure the resultant work/set times for their respective initiator systems, such as described above, the results of which are illustrated in Table 11.

TABLE 11

| Ex. | Combine Exs. | Thiourea wt % in part A | hydroperoxide wt % in part B | Catalyst wt % input A | Work/Set Time (seconds) |
|---|---|---|---|---|---|
| 24 | 20 + 21 | BTU (1.82%) | CHP (2.85%) | 3% Ex. 1A | 300/390 |
| 25 | 20 + 22 | TTU (1.82%) | CHP (2.85%) | 3% Ex. 1A | 130/160 |
| 26 | 20 + 23 | PTU (1.82%) | CHP (2.85%) | 3% Ex. 1A | 60/80 |

As is illustrated in Table 11, good work/set times are achieved for a variety of thiourea compounds when copper is included, with TTU and PTU providing excellent results.

Examples 27 to 44

Resins containing hydroperoxides are made into the compositions listed in Table 12. All components are mechanically mixed or magnetically stirred to form homogeneous mixtures or solutions.

TABLE 12

| (in parts) | Ex. 27R | Ex. 28R | Ex. 29R | Ex. 30R | Ex. 31R |
|---|---|---|---|---|---|
| E6BAD | — | — | 20.0 | — | — |
| BisGMA-TEGDM | 39.0 | 39.0 | 15.0 | 39.0 | 39.0 |
| TEGDM | 10.0 | 10.0 | 18.0 | 10.0 | 10.0 |
| UDMA | 5.0 | 5.0 | 9.0 | 5.0 | 5.0 |
| EBPADM | 36.0 | 36.0 | 34.62 | 36.0 | 36.25 |
| EDMAB | 0.4 | 0.4 | 0.2 | 0.4 | 0.4 |
| CQ | 0.2 | 0.2 | 0.08 | 0.2 | 0.2 |
| BYK W9010 | 0.3 | 0.3 | 0.5 | 0.3 | 0.3 |
| BHT | 0.1 | 0.1 | 0.1 | 0.1 | 0.1 |
| CHP | 2.0 | 2.5 | 2.5 | 3.0 | 1.75 |

The resin examples above are used to prepare the following paste compositions listed in Table 13. All components are mixed and dispersed with the aid of a 3-roll mill.

TABLE 13

| (in parts) | Ex. 27 | Ex. 28 | Ex. 29 | Ex. 30 | Ex. 30 |
|---|---|---|---|---|---|
| Resin | 33.2 (Ex. 27R) | 33.2 (Ex. 28R) | 29.0 (Ex. 29R) | 33.2 (Ex. 30R) | 33.2 (Ex. 31R) |
| GM27884-K6 | 61.1 | 61.1 | 61.0 | 61.1 | 61.6 |
| YbF3 | 4.7 | 4.7 | 9.0 | 4.7 | 4.7 |
| R202 | 1.0 | 1.0 | — | 1.0 | 0.5 |
| R812S | — | — | 1.0 | — | — |

Resins containing thiourea compounds are made into the compositions listed in Table 14. All components are mechanically mixed or magnetically stirred to form homogeneous mixtures or solutions.

TABLE 14

| (in parts) | Ex. 32R | Ex. 33R | Ex. 34R | Ex. 35R | Ex. 36R |
|---|---|---|---|---|---|
| E6BAD | — | 22.0 | — | — | — |
| BisGMA-TEGDM | 39.0 | 16.5 | 39.0 | 39.0 | 39.0 |
| TEGDM | 10.0 | 19.8 | 10.0 | 10.0 | 10.0 |
| UDMA | 5.0 | 9.9 | 5.0 | 5.0 | 5.0 |
| EBPADM | 36.0 | 29.41 | 36.0 | 36.0 | 36.0 |
| SR-494 | 7.0 | — | 7.0 | 7.0 | 7.0 |
| EDMAB | 0.4 | 0.2 | 0.4 | 0.4 | 0.4 |
| CQ | 0.2 | 0.08 | 0.2 | 0.2 | 0.2 |
| BYK W9010 | 0.3 | 0.5 | 0.3 | 0.3 | 0.3 |
| BHT | 0.1 | 0.11 | 0.1 | 0.1 | 0.1 |
| PTU | 1.5 | 1.5 | 3.0 | 4.0 | 5.0 |

The resin examples above are used to prepare the following paste compositions listed in Table 15. All components are mixed and dispersed with the aid of a 3-roll mill.

TABLE 15

| (in parts) | Ex. 32 | Ex. 33 | Ex. 34 | Ex. 35 | Ex. 36 |
|---|---|---|---|---|---|
| Resin | 33.2 (Ex. 32R) | 26.65 (Ex. 33R) | 33.2 (Ex. 34R) | 33.2 (Ex. 35R) | 33.2 (Ex. 36R) |
| GM27884-K6 | 61.1 | 61.4 | 61.4 | 61.4 | 61.4 |
| YbF3 | 4.7 | 9.0 | 4.7 | 4.7 | 4.7 |
| R812S | 1.0 | 1.0 | 0.7 | 0.7 | 0.7 |
| Ex. 1A | — | 1.75 | — | — | — |

The two-part paste examples containing either a chemical reductant or oxidant compound above are combined to measure the resultant work/set times for their respective initiator systems, e.g., as described above, with the illustrative results set forth in Table 16.

TABLE 16

| Ex. | Combine | Thiourea wt % in part A | hydroperoxide wt % in part B | Catalyst wt % inpart A | Work/Set Time (seconds) |
|---|---|---|---|---|---|
| 37 | 27 + 32 | PTU (1.5%) | CHP (2.0%) | — | 180/205 |
| 38 | 28 + 32 | PTU (1.5%) | CHP (2.50%) | — | 160/185 |
| 39 | 29 + 33 | PTU (1.5%) | CHP (2.50%) | 1.75% Ex. 1A | 90/120 |
| 40 | 30 + 32 | PTU (1.5%) | CHP (3.0%) | — | 120/140 |
| 41 | 4 + 9 | PTU (2%) | CHP (2.50%) | — | 120/140 |
| 42 | 31 + 34 | PTU (3%) | CHP (1.75%) | — | 130/145 |
| 43 | 31 + 35 | PTU (4%) | CHP (1.75%) | — | 105/125 |
| 44 | 31 + 36 | PTU (5%) | CHP (1.75%) | — | 85/105 |

As illustrated in Table 16, good work/set times are achieved using PTU and CHP in combination, with the best results being obtained for compositions comprising higher concentrations of PTU+CHP and/or for compositions comprising copper (II).

Example 45

In addition, good physical parameters are obtained for composites prepared according to the preceding examples. For example, filling of deep cavities results in good adhesion of the restoration material to a substrate, without the formation of voids between the restoration material and substrate, such as illustrated in FIG. 1, whereas use of competitive materials results in very poor adhesion to the substrate, particularly at the bottom of the cavity (which is 7 mm in depth), with void formation. In addition, interproximal leakage is not observed for restoration material composites prepared using compositions provided herein, as illustrated in FIG. 2, whereas competitive light curing bulk fill composite materials result in microleakage along interproximal margins.

In addition, composites described in the preceding examples provided good physical parameters, such as having very low volume shrinkage upon curing (e.g., less than 5%), good flexural strength (e.g., greater than 100 MPa), good compression strength (e.g., greater than 150 MPa), good diametral strength (e.g., greater than 30 MPa), low water absorption (e.g., less than 20 µg/mm$^3$), good water solubility (e.g., less than 1 µg/mm$^3$), and good radiopacity (e.g., greater than 300% Al).

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A method for restoring a tooth in an individual, the process comprising:
   a. combining a first composition with a second composition to form a mixed composition,
   the first composition comprising a hydroperoxide and a copper (II) compound, the second composition comprising a thiourea and a copper (II) catalyst, and one or both of the first and/or second compositions comprising a polymerizable monomer and a filler, the polymerizable monomer comprising an ethylenic group;
   b. filling in bulk a cavity of the individual with the mixed composition; and
   c. curing the mixed composition under ambient conditions,
   wherein the mixed composition further comprises Ytterbium Fluoride (YbF3), and the mixed composition is hardened to have a radiopacity of greater than 300% aluminum, wherein upon curing the total volume of the mixed composition within the cavity shrinks by less than 5%, wherein flexural strength is greater than 100 MPa, compression strength is greater than 150 Mpa, wherein diametral strength is greater than 30 Mpa, wherein the mixed composition further comprises an acid, wherein the amount of acid is less than 1 wt. % acid, relative to the weight of the mixed composition excluding weight of the filler, wherein the curing occurs in about 2 minutes or less, and wherein the cavity has a depth of at least 5 mm.

2. The method of claim 1, wherein the cavity is a Class I cavity.

3. The method of claim 1, wherein the cavity is a Class II cavity.

4. The method of claim 1, wherein upon curing of the mixed composition within the cavity, a microleakage-free filling is formed therein.

5. The method of claim 1, wherein the mixed composition comprises less than 0.5 wt. % acid, relative to the weight of the mixed composition excluding weight of the filler.

6. The method of claim 1, wherein the hydroperoxide is a tertiary aryl hydroperoxide.

7. The method of claim 1, wherein the hydroperoxide is cumene hydroperoxide.

8. The method of claim 1, wherein the thiourea is pyridyl thiourea.

9. The method of claim 1, wherein upon combination of the first composition and the second composition, the combined weight of the thiourea and the hydroperoxide constitute less than 10% (w/w) of the mixed composition, relative to the monomer.

10. A method for restoring a tooth in an individual, the process comprising:
    a. combining a first composition with a second composition to form a mixed composition,
    the first composition comprising a tertiary hydroperoxide and a copper (II) compound,
    the second composition comprising pyridyl thiourea and a copper (II) catalyst, and one or both of the first and/or second compositions comprising a polymerizable monomer and a filler, the polymerizable monomer comprising an ethylenic group, upon combination of the first composition and the second composition, the combined weight of the thiourea and the hydroperoxide constituting less than 10% (w/w) in the mixed composition, relative to the monomer,
    the mixed composition further comprises an acid, wherein the amount of acid is less than 1 wt. % acid, relative to the weight of the mixed composition excluding weight of the filler;
    b. filling in bulk a cavity of the individual with the mixed composition; and
    c. curing the mixed composition to form a microleakage free filling within the cavity, the volume of the mixed composition shrinking by less than 5% during curing wherein the mixed composition further comprises Ytterbium Fluoride (YbF3), and the mixed composition is hardened to have a radiopacity of greater than 300% aluminum, wherein flexural strength is greater than 100 MPa, compression strength is greater than 150 Mpa, wherein diametral strength is greater than 30 Mpa, wherein the curing occurs in about 2 minutes or less, and wherein the cavity has a depth of at least 5 mm.

11. The method of claim 10, wherein the cavity is a Class II cavity.

* * * * *